United States Patent [19]

Howland

[11] Patent Number: 5,034,011

[45] Date of Patent: Jul. 23, 1991

[54] SEGMENTAL INSTRUMENTATION OF THE POSTERIOR SPINE

[75] Inventor: Robert S. Howland, Seal Beach, Calif.

[73] Assignee: Advanced Spine Fixation Systems Incorporated, Stanton, Calif.

[21] Appl. No.: 565,266

[22] Filed: Aug. 9, 1990

[51] Int. Cl.$^5$ .................. A61F 5/04; A61F 5/00; A61F 2/44

[52] U.S. Cl. ..................... 606/61; 606/72; 606/73; 128/69; 623/17

[58] Field of Search ............ 606/61, 59, 57, 65, 606/72, 73, 105; 128/69; 623/16, 17

[56] References Cited

U.S. PATENT DOCUMENTS

| | | | |
|---|---|---|---|
| 4,361,141 | 11/1982 | Tanner | 128/69 |
| 4,382,438 | 5/1983 | Jacobs | 606/61 |
| 4,411,259 | 10/1983 | Drummonds | 606/61 |
| 4,422,451 | 12/1983 | Kalamchi | 128/69 |
| 4,433,677 | 2/1984 | Ulrich | 128/69 |
| 4,569,338 | 2/1986 | Edwards | 606/61 |
| 4,653,481 | 3/1987 | Howland | 128/69 |
| 4,655,199 | 4/1987 | Steffee | 606/61 |
| 4,771,767 | 9/1988 | Steffee | 606/61 |
| 4,854,304 | 8/1989 | Zielke | 128/69 |

FOREIGN PATENT DOCUMENTS 3802833 9/1988 Fed. Rep. of Germany ........ 606/61

Primary Examiner—Robert A. Hafer
Assistant Examiner—Michael Brown
Attorney, Agent, or Firm—Beehler & Pavitt

[57] ABSTRACT

Improved instrumentation of the posterior spine includes a threaded screw for insertion into the sacrum, threaded adjusting rods and intravertebral hook device on the end of the adjusting rod. One end of the adjusting rod includes a pivotal clevis assembly and an automatic safety interlock for securing the clevis assembly to the screw. The receiving end of the bone screw includes spaced arms to receive the clevis which is inserted and rotated to a locking position. Thereafter, the hooks are positioned on the lamina and the adjusting rod is adjusted for compression or distraction. The hex area on the adjusting rods are then safety wired. The generally triangular orientation provides added strength and a wider foot print attachment which will resist rotational forces. Also disclosed is an improved bone screw which facilitates placement of a bone cement in the desired location.

14 Claims, 3 Drawing Sheets

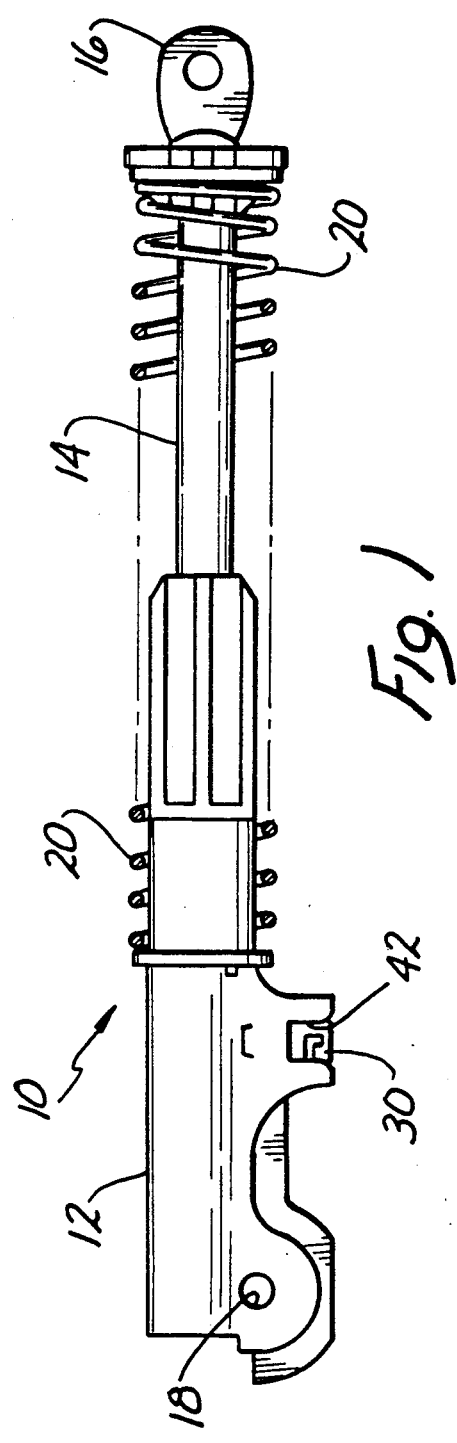
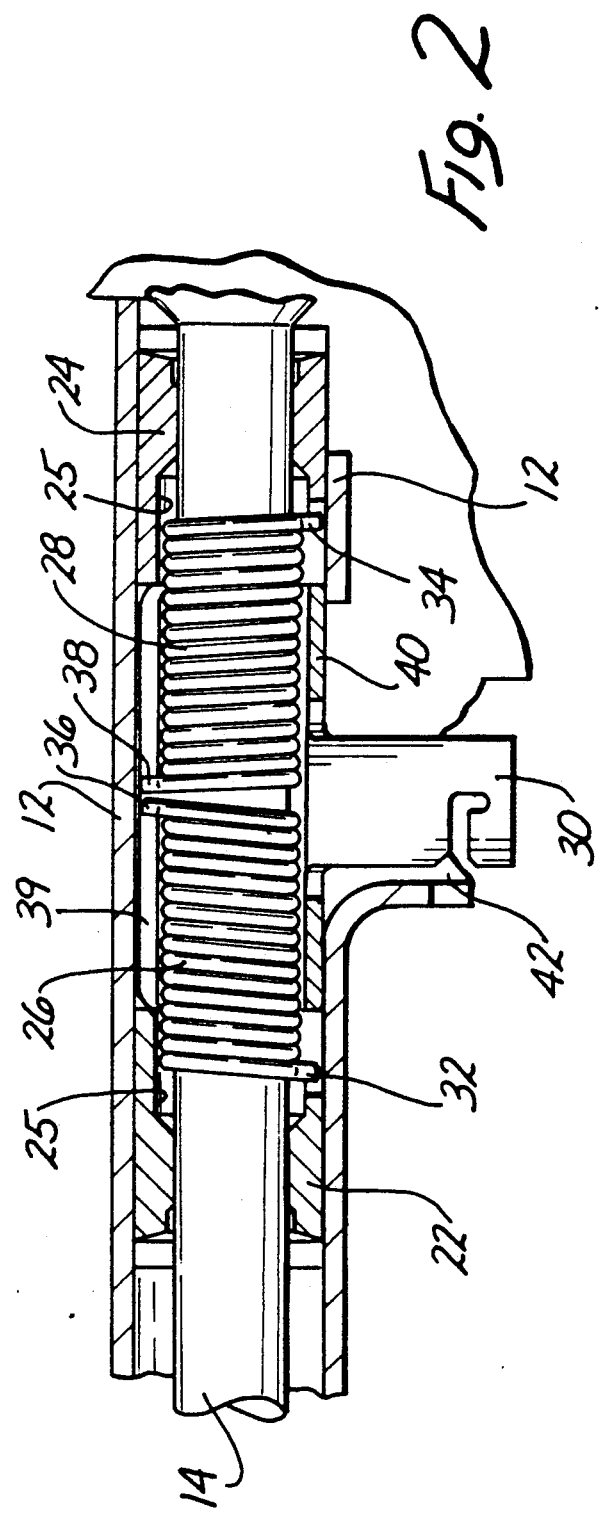

SEGMENTAL INSTRUMENTATION OF THE POSTERIOR SPINE

RELATED PATENTS AND APPLICATIONS

Reference is made to U.S. Pat. No. 4,653,481 issued on Mar. 31, 1987 and to U.S. patent application Ser. No. 07/501,742 filed on Mar. 29, 1990 and each assigned to the same assignee.

FIELD OF INVENTION

The present invention relates to instrumentation of the posterior spine and more particularly to improved instrumentation of the posterior spine for use in those instances in which additional internal support and compression or distraction is needed during the fusion process and to an improved bone screw for use in implant systems, especially those of the spine and sacrum.

DESCRIPTION OF THE PRIOR ART

The above identified patent describes the prior art and the prior approaches with respect to implantable spinal fixation systems and reference is made to that disclosure which is incorporated herein by reference. Reference is also made to the prior patents disclosed in the above identified patent.

In addition to the above and as noted in the above identified application, there are systems known as the Syracuse system, the Luque system (Luque, Clinical Orthopaedics and Related Research, Number 203, February, 1986, Pp 126-134), the Vermont system, the Puno system, the Cotrel-Duboset system (Cotrel et al, Clinical Orthopaedics and Related Research, Number 227, February, 1988, Pp 10-23), the Harrington system (Harrington, Clinical Orthopaedics and Related Research, Number 227, February, 1988, Pp 3-5), the Edwards system, the Zielke system (Zielke et al, Clinical Orthopaedics and Related Research, Number 203, February, 1986, Pp 151-152), the AO system and the Knodt system (Selby, Clinical Orthopaedics and Related Research, Number 203, February, 1986, Pp 179-184).

In the past, sacral attachment with hooks proved difficult to accomplish, for example with a Knodt distraction rod system. Adjusting rods and hooks were usually closely aligned causing adjustment of engagement to be difficult. In some instances, the prior systems required large distractions to hold the system in place which in turn tended to cause loss of lordosis. In addition, these prior art systems had a relatively high profile which tended to cause patient pain.

There is a need for methods of stabilizing the lumbar spine, especially in case of degenerative lumbar scoliosis, degenerative spondylolisthesis and spinal stenosis. These conditions commonly require decompression because of stenosis. With decompression, an already unstable spine is made very much more unstable and fusion is necessary. However, fusion alone without some form of added internal fixation is prone to failure in many instances. Pseudarthrosis may occur, in which cases deformities may result. In addition, it is often necessary to reduce, at least partially, the existing deformity. Again, this requires internal fixation. Such procedures as vertebrectomy or spinal osteotomy usually require reinforcement with a fixation device. The use of sacral screws, adjusting rods, and hooks for internal fixation purposes has now become a valuable adjunct to spine surgery.

In addition, there are instances in which bone screws, such as cancellous bone screws, sacrum screws and pedicle screws are inserted into a bony member and for any number of reasons, the screw is not firmly anchored in place. Typically a bone cement is used to achieve secure attachment of the screw to the surrounding bone. In spine cases, it is sometimes difficult to place the bone cement in the proper location because of the nature of the spinal construction.

A need also exists for a system which offers more secure attachment, especially in the case of adjusting rods to the S1 segment. In degenerative diseases, this is critical. In the past, fixation has not been secure and tearing lose of the sacral attachment has been distressingly frequent. In order to gain a more secure attachment to the pelvis, rods have been bent and driven across the sacroiliac joint a procedure Which may damage the joint and which often produces pain.

There is also a need for instrumentation which may be securely attached and remain securely attached over the period of use. For example, recent data tend to indicate that bone fusion on the average will start to progress in patients 30 to 90 days after a sacral lumbar instrumented fusion operation is performed. Following surgery, the patient is generally ambulatory and the support provided by the instrumentation should be capable of remaining in place and effective for a period which may be as long as 8 months or more.

It is thus apparent that a need exists for instrumentation which may be securely anchored in place and remain in place for extended periods of time, providing the requisite stabilization and support during fusion, and which instrumentation offers special advantages.

In the case of bone screws of the type described, there is a need for a relatively simple, but effective structure which permits the effective use of bone cement delivered to the precise location needed and which promotes secure fixation of the instrumentation.

A need also exists for improved instrumentation which may be implanted in less time than other types of spinal fixation devices.

A need also exists for improved segmental instrumentation of the posterior spine, useable to provide either compression or distraction, and which is relatively easy to install, effectively locked in place and which provides the needed support over that period of time required for bone fusion.

In particular, a need exists for an implantable compression and distraction system for use in the posterior spine in which the distraction or compression rods are firmly anchored in place and remain in place once properly installed.

BRIEF DESCRIPTION OF THE INVENTION

The above and other objects are achieved in accordance with this invention by the provision of improved segmental instrumentation of the posterior spine and an improved bone screw structure.

The basic instrumentation includes threaded sacral bone screws, threaded adjusting rods, and intravertebral hook means received on the one end of the adjusting rod. The end of the adjusting rod which is mounted on the sacral bone screw includes a pivotal clevis assembly and an automatic safety interlock through the use of a unique sacrum screw and clevis assembly to secure the adjusting rod and the hook to the bone screw. The details of a preferred procedure for assembly of the instrumentation to a patient will be described later. The system provides for either compression or distraction, as may be required, secure fixation and reliable relatively long term stabilization and support. Due to the relatively simple, but effective mounting of the pivotal clevis to the sacrum screw, the overall time for installation is markedly reduced over prior procedures and prior instrumentation.

Typically, bone screws are placed into the S1 location of the sacrum. Adjustment rods are then assembled to the bone screws, in this case sacrum bone screws. One end of each adjustment rod includes the pivotal clevis assembly and the other end of each of the adjustment rods includes lamina hooks, either compression or distraction hooks, which are placed onto the lamina. The adjustment rod normally has preassembled to it the pivotal clevis and the lamina hook thus forming an adjustment rod assembly that is mounted on the sacrum screw as a unit. The result is a generally triangular support structure in which the base is formed by the spaced sacral screws, the sides by the adjustment rods which carry the lamina hooks, the latter normally spaced closer together than the sacrum screws. Each adjustment rod is then adjusted to provide the desired compression or distraction. Thereafter, the nut on the adjusting rods are safety wired together to prevent relative rotation, and installation of the relatively low profile system is complete.

One end of the sacrum screw is threaded for insertion into the sacrum and the other end of the screw is provided with a unique self-locking structure. This self-locking structure cooperates with the pivot clevis on the end of the adjusting rod such that clevis is just slipped into place and pivoted automatically to lock the clevis and the one end of the adjusting rod to the sacrum screw. The mounting end of the sacrum screw is thus provided with spaced clevis receiving arms forming a slot therebetween and with an inclined locking face in the slot and between the arms. The clevis includes a pivot pin which is pivotable with respect to the clevis and defines an axis of rotation of the clevis. The clevis also includes an inclined locking face cooperating with the locking face of the sacrum screw such that only in one relative orientation of the respective faces, when the respective faces are in spaced parallel relation, the clevis may be assembled to the sacrum screw and automatically locked in place.

The side arms of the sacrum screw each include slotted tracks having portions which are angled essentially at the same angle as the inclined locking face between the arms. The dimension between the locking face of the clevis and the axis of the pivot pin is such that pivot pin can enter the slotted track portions with the respective locking surfaces being disengaged. The sacrum screw slotted tracks each include a second angled portion and ear sections, the second angled portion operating to guide the pivot pin to effect a small displacement between the opposed locking faces by causing the pivot pin of the clevis to move away from the locking surface of the sacrum screw.

The body of the clevis on the leading and trailing side of the locking face includes walls whose dimension relative to the axis of the pivot pin is greater than the dimension from the axis of the pivot pin to the locking surface on the clevis. Thus, with the opposed locking surfaces other than in parallel spaced relation, the ears overly and prevent the pivot pin from moving other than along the tracks. Since one portion of the tracks is parallel to the locking surface between the arms, the pivot pin cannot move to an unlock position since there is insufficient clearance between the leading and trailing walls of the clevis and the locking face of the sacrum screw to permit the clevis to be unlocked, save for the one relative orientation in which the locking surfaces are in spaced parallel relation. In effect, the clevis which is rotatable relative to the sacrum screw is locked to the sacrum screw in all relative positions but one. This represents a simple but highly effective interlock which permits rapid installation of the system and which remains securely locked after installation.

The adjusting rod includes a nut in the center section and the clevis is mounted on one end of the rod while hook means are threaded on the other end of the rod. In installation, the sacrum screws are placed in the sacrum, the adjusting rod with the clevis on one end and the hook on the other end is locked to the sacrum screw and the hook is properly located on the lamina. The hook may be a compression hook or a distraction (decompression) hook. The length of the adjusting rod and thus the distance between the clevis and the hook is adjusted by the nut which also rotates the rod to increase or decrease the effective length thereof between the clevis and hook, and thereafter the nuts are safety wired together. In either case, it is important to assure that enough of the length of the threaded end of the adjusting rod remains threaded to the associated clevis or hook. Thus, each of the clevis and hook are provided with an inspection aperture so that the threaded rod may be seen.

In some cases due to prior surgery or diseased bone or for other reasons, it is sometimes necessary to use a bone cement to assure firm and secure fastening of the screw to the bone. One aspect of this invention involves the use of an axial bore in the screw which extends at least partly into the threaded end. Axially displaced transverse passages are provided which communicate with the bore so that the surgeon may inject a bone cement, such as flowable methyl methacrylate and the like, into the axial bore using a hypodermic syringe. This effectively places the bone cement precisely where needed, between the screw thread and the surrounding bone structure. In effect, the cement can travel in any space between the threads and the surrounding bone, precisely the area in which the cement should be placed.

The present invention has helped to establish the mechanical safety of the sacral screw attachment, distraction rods and lamina hooks. With this invention, a wide triangular base is formed at assembly. This wide base allows greater support against rotational forces and increased ease of adjustment. With the safety interlock system associated with the sacral screw, dislocation will be eliminated. Since firm sacral attachment controls rotational forces and hook migration, only small distraction adjustment need be made to correct a patient's condition. This reduces the need for large distractions to hold the system in place which heretofore has tended to cause loss of lordosis. The system of this invention also has a low profile for this area of the spine. The surgery will have less complexity, reduced operation time and increased implant efficiency.

It is apparent from the foregoing brief description that the present invention offers many advantages over the prior art spinal fixation systems and methodology. These and other advantages and other objects are made more clearly apparent from a consideration of the several forms in which the invention may be embodied.

Such forms are illustrated and described and are for the purposes of illustration of the general principles of this invention; but it is understood that the detailed description which follows is not to be taken in a limiting sense.

DESCRIPTION OF THE DRAWINGS

FIG. 2 is an enlarged side view of a sacral bone screw in accordance with this invention;

FIG. 2a is a view as seen from the left of FIG. 2;

FIG. 7 is a side view of a compression hook in accordance with this invention;

FIG. 8 is a fragmentary view, in perspective, of an adjusting rod in accordance with this invention.

DETAILED DESCRIPTION OF THE INVENTION

Figure 1:
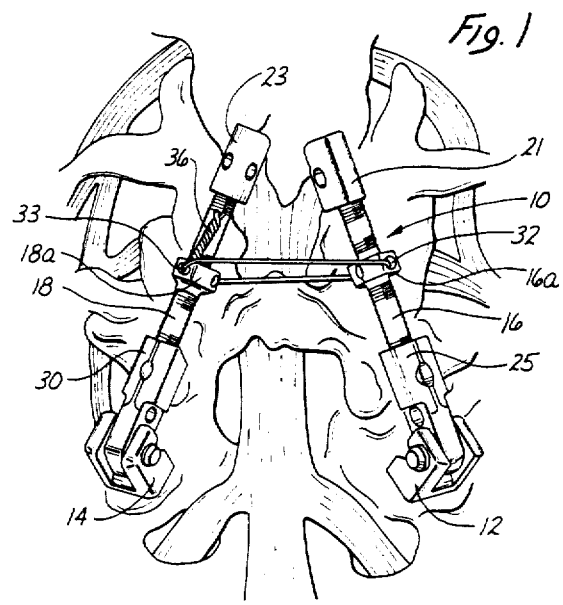
FIG. 1 is a diagrammatic view of the segmental instrumentation of this invention is an installed condition.

Referring to the drawings which illustrate preferred forms of the present invention, FIG. 1 illustrates a segmental instrumentation 10 in accordance with this invention. In the form shown, for illustration purposes only, the instrumentation is shown in the installed condition in the posterior spine and includes sacral bone screws 12 and 14 in the S1 location of the sacrum. If needed spacers as described in the above identified application may be used with the bone screws. Mounted on each of the bone screws is a threaded adjustment rod 16 and 18, respectively. Each adjustment rod includes a hexagonal nut 16a and 18a preferably formed integrally with the rod.

One end of each rod has threaded thereon an intravertebral lamina hook 21 and 23, while the other end has threaded thereon a pivotal clevis assembly 25 and 30. The lamina hooks are placed over the lamina. The pivotal clevis assemblies are basically of the same structure while the hooks, illustrated as distraction hooks, may be a left hand and a right hand hook, as will be described. The hexagonal nuts include safety wire apertures 32 and 33 therethrough and through the rod for a safety wire 35 which is inserted and twisted as at 36 to prevent relative loosening of the respective rods with respect to each other and to insure that the lamina hooks do not dislocate from the lamina independently.

The installation of the system of this invention as illustrated in FIG. 1 involves placing the sacrum screws in the spaced orientation in the sacrum as shown. Thereafter, the adjusting rods with the hooks and clevises threaded thereon are mounted to the sacrum screws. The hooks are then located on the lamina and the rod adjusted by turning the rod nut. The safety wire is then installed. As seen, a generally triangular configuration is provided in which the sacrum screws form the base of the triangle and the rods form the legs. The distance between the sacrum screws is greater than the distance between the hooks. This structure provides the advantages previously noted. Moreover, the profile of the installed instrumentation is relatively low as is apparent from the illustration.

Figure 3:
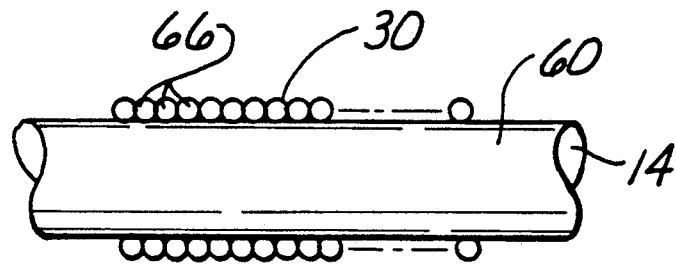
FIG. 3 is an enlarged side view of the mounting end of the sacral bone screw of FIG. 2.

Referring now to FIGS. 2, 2a and 3, the structure of the improved sacrum screw 12 is shown, it being understood that the structure of screw 14 is the same. The term "sacrum screw" is used for convenience since the screw may be installed in any other bony structure. The screw 12 includes a threaded end 40 and a mounting end 45, the latter receiving whatever component is to be assembled to the screw. The length of the threaded end may vary from 30 to 45 mm, for example, while the major diameter may vary from 6.5 to 7.4 mm with a minor diameter in the range of from 4.2 to 4.75 mm. The thread is a helical thread of 9 threads per inch, for example, having the major and minor diameters noted. As shown, there is a valley 46 between adjacent crests. The forward end 47 of the threaded end may be in the form of a pilot to guide and center the screw in a drilled hole in a bone structure during installation.

Between the threaded end 40 and the mounting end 45 there is a a tapered transition section 49 for mating with a spacer, as described in the application referred to, if a spacer is needed.

The mounting end 40 of the screw includes spaced clevis receiving arms 50 and 51 with a slot 55 between the arms. The base of the slot 55 includes an inclined locking face 57 composed of two correspondingly oppositely inclined locking face surfaces 57a and 57b. Each of the side arms 50 and 51 includes a slotted track 60 of a compound configuration relative to the locking face 57. The slotted track 60 includes an open end 62 defined by two opposed track faces 62a and 62b each of the same predetermined angle and which faces are in essentially spaced parallel relation to the surface of locking face surface 57a. The dimension between the opposed track faces is such as to permit sliding passage of the clevis pin of the clevis assembly, to be described, i.e., the dimension between the faces and the diameter of the clevis pin permits a sliding passage without excessive motion between the outside surface of the pin and the receiving faces.

Each of the tracks 60 also includes a locking track section 65 inclined at an angle different from that of the track faces 62a and 62b forming the open end of the tracks. Thus, the track sections 65 each include a closed end 65a, preferably circular in section, and locking track faces 65b and 65c in spaced parallel relation and oriented at an angle different from that of faces 62a and 62b. Accordingly, each arm includes an ear 70, the end 71 of which overlies the centerline 73 of the circle or other geometry forming the closed end 65a. The result is that an elongated cylinder may enter the open end of the tracks and change direction of travel as guided by the locking track faces. Similarly, travel of the elongated cylinder from the closed end 65a along the faces 65b and 65c requires that the center axis of the cylinder be displaced so that the cylinder may enter the space between track faces 62a and 62b and at the same time clear the ear 70 and the end 71 thereof.

Figure 4:
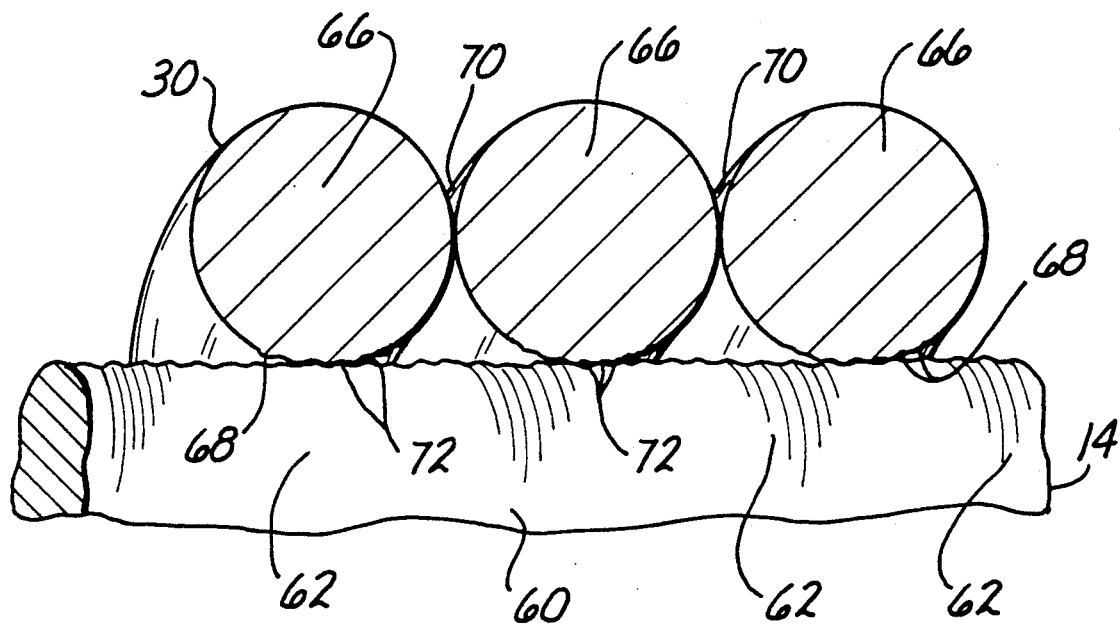
FIG. 4 is a view partly in section and partly in elevation of a pivotal clevis assembly in accordance with this invention.
Figure 5:
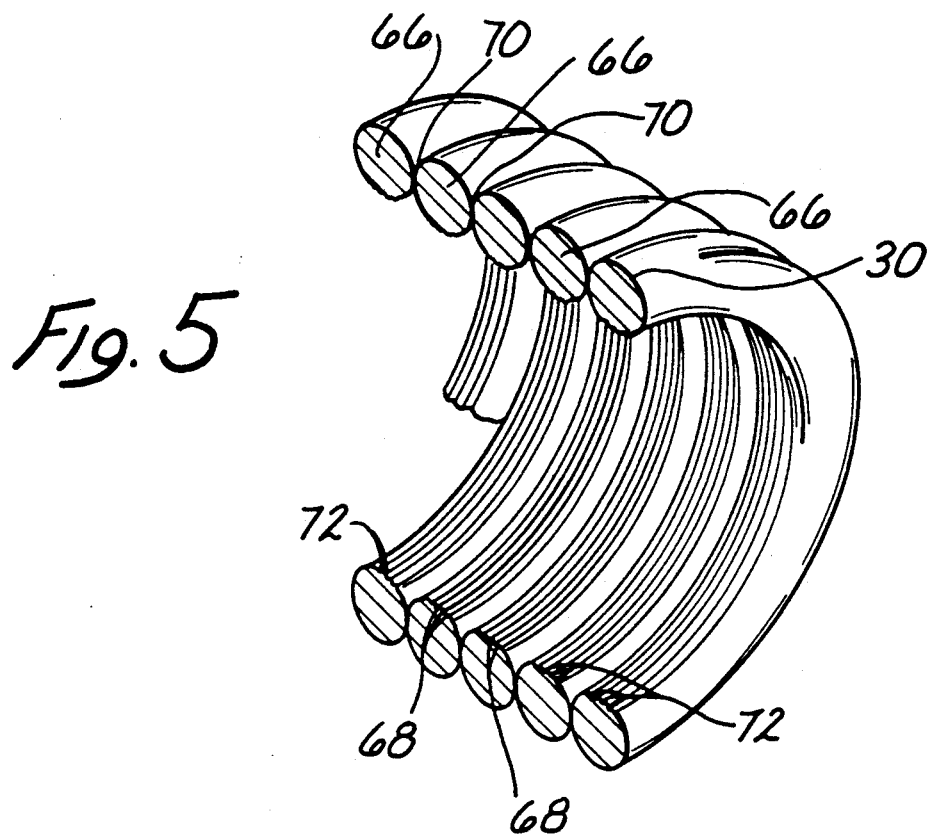
FIG. 5 is a view partly in section and partly in elevation illustrating the configuration of the body of the clevis assembly absent the pivot pin, in accordance with this invention.

The mounting end of the screw forms a part of an automatic locking system, the other portion of which is the clevis assembly. Referring to FIGS. 4 and 5, the details of the clevis assembly 25 and 30 are illustrated, it being understood that the basic structure of each is the same, except that the overall length may vary. Accordingly, the description will be made with reference to clevis assembly 25, the latter including a body section 75 preferably having an outer hexagonal configuration for use of tooling as may be required. Preferably integrally formed with the body section 75 is a clevis end 77, the latter preferably less in cross-sectional dimension than the body section and including a pivot pin aperture 80 spaced from the end 81 of the body section. Both the body section and the clevis end are threaded to receive the threaded section of the adjusting rod to be described.

Received in the pivot pin aperture 80 is a pivot pin 85 (FIG. 4), the pin being preferably rotatable relative to the clevis end 77 of the clevis assembly. Each end of the pin is provided with a guide nubbin 86 and 87 and a center retaining band 90 composed of spaced shoulders 90a and 90b with a valley 90c between the shoulders. The pivot pin is staked by the use of a blunt punch to the clevis end as indicated at 90d permitting the pin to rotate but securing it in place. The distance between the nubbins 86 and 97 and the respective facing shoulders 90a and 90b is coordinated with the cross-section of the arms 50 and 51 such that the pivot pin may be assembled to the clevis, and restrained against sideways movement. Each of the clevis end 77 and the body section 75 is provided with an inspection window 92 and 93 so that the location of the end of the threaded adjusting rod may be seen to determine the position thereof.

Referring now to FIG. 5, the clevis end 77 of the clevis assembly is uniquely configured to lock automatically with the clevis arms 50 and 51. Thus, the clevis end includes a flat face 95 with adjacent curved faces 96 and 98. The dimension from the centerline 100 of the pivot pin aperture 80 to the flat face 95 is less than the dimension from the same centerline to the curved surfaces 96 and 98 and the adjacent side walls 96a and 98a. Thus, with the flat face 95 of the clevis end in spaced parallel relation to the locking face surface 57a on the mounting end of the screw, the pivot pin may be inserted between track faces 62a and 62b of each of the arms 50 and 51. In this relative position, the clevis assembly is oriented at an angle approximately corresponding the angle of locking face surface 57a and the nubbins are on the outboard sides of the arms.

As the pivot pin is moved to the locking track section 65 of each arm, the result is that the flat face 95 is displaced a small amount vertically relative to the locking face surface 57a due to the inclined angle of locking track faces 65b and 65c of each arm. As the pivot pin 90 reaches the closed end 65a of the locking track, the clevis assembly can be rotated clockwise or counterclockwise, depending upon screw orientation, to achieve automatic locking.

Automatic locking is achieved in all relative orientations of the flat face 95 and the locking face surface 57a other than a parallel relation, i.e., that orientation needed to insert the clevis into the mounting end of the screw. The normal installed orientation of the clevis relative to the screw is such that they are in a roughly relative right angle orientation. Since the dimension between the centerline of the pivot pin and the surfaces 96, 96a, 98 and 98a is greater than the clearance between the centerline 105 of the closed end 65a of the track sections, and because of the overhanging end 71 of the ear 70 and the angle of track faces 65b and 65c, the pivot pin cannot travel out of the locking track 65. However, if the clevis is rotated such that the flat face 95 is approximately parallel to locking face surface 57a, there is sufficient clearance for the pivot pin to clear the end 71 of the ear and to travel down the track faces 65b and 65c.

It is apparent that the self-locking feature vastly simplifies installation of the clevis assembly and the associated adjusting rod and the hook mounted on the other end of the threaded adjusting rod. It is also apparent that, save for one specific orientation, the clevis is locked in place but free to rotate to whatever position may be desired.

Figure 6:
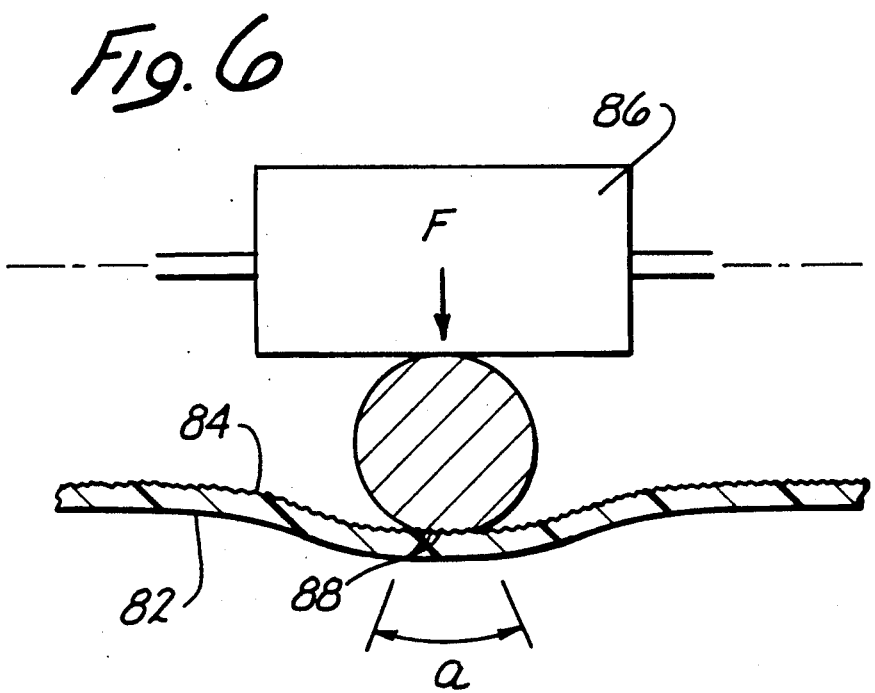
FIG. 6 is a side view of a distraction hook in accordance with this invention.

Referring to FIGS. 6 and 7, a distraction hook 110 and a compression hook 120, respectively, are illustrated. The hooks are generally of the same overall configuration, but they are not identical. Distraction hook 110 includes a body 122 internally threaded at one end with an inspection aperture 124 therein so that the position of the end of the adjusting rod may be ascertained. The hook also includes a hook section 125 forming an arcuate opening 128 for mounting on the desired location on the lamina. In order to reduce the profile of the hook, as installed, there is a right and left hand hook in which the hook section 125 is tilted to the right or left of the body 122, as seen from the left of FIG. 6. In effect, the nose end 130 of the hook between the line 131 and end 132 is right or left oriented.

The compression hook 120 also includes a body 135, internally threaded for the distraction rod and is provided with an inspection aperture 138 therein so that the position of the end of the adjusting rod may be ascertained. The hook also includes a hook section 140 forming an arcuate opening 142 for mounting on the desired location on the lamina. In the case of the compression hook, the lower surface 144 of the arcuate opening is inclined, as shown.

To reduce hook displacement during installation and adjustment rod rotation during assembly in a patient, the components of the instrumentation are supplied as a right and left side assembly. In the left side assembly, the adjusting rod is preferably arranged such that the left hand threaded portion is closer to the hook while the right hand threaded portion is closer to the clevis. The right side assembly has the adjusting rod preferably arranged such that the right hand threaded portion is closer to the hook and the left hand side is closer to the clevis, i.e., just the reverse of the left side assembly.

When adjusting the adjusting rods, the left side rod is rotated clockwise and the right side rod is rotated counterclockwise. Using the methodology, the rotational torque will cause the hook area to apply pressure on the under side of the lamina laterally. Because the lamina tapers wider away from the spinous process, this method of assembly and adjustment will offer added resistance to hook displacement.

FIG. 8 illustrates the adjustment rod 16 or 18, each of which is essentially of the same structure. Thus, reference will be made to rod 16. In approximately the center of the rod 16 is the adjusting nut 16a which, for example, may be hexagonal. The threads on one side 151 may be right hand threads and the threads on the other side 153 may be left hand threads, one end having a clevis assembly screwed thereon and the other end having a hook threaded thereon. As the nut 16a is rotated in one direction, the distance between the hook and the clevis increases and when the nut is rotated in the opposite direction, the distance decreases. Since the system may be used for compression or distraction, the screws may be in different orientations for each procedure.

For example, as seen in FIG. 1, the system is a distraction system with the open end of the tracks facing the hook and the pivot pin bearing against the closed end 65a. In a compression installation, the open end of the tracks face away from the hook and the pivot pin again bears against the closed end 65a.

Following installation and appropriate adjustment, a safety wire is installed in the aperture 32 of the nut and in aperture 33 or nut 18a. To facilitate wire installation, there are apertures extending through each face of the nut to an opposite face.

As is apparent, in the case of bone screws there may come a circumstance wherein the bone screw is not firmly anchored in a stable bone structure. The instability may be the result of any number of source problems, e.g., diseased bone or bone of less density as compared to adjacent regions. To increase screw retention in the bone, a bone cement is used, normally after the screw is placed into the bone. One of the practical problems in using a bone cement is to have it placed where it is needed and not have flow other than where needed. In accordance with this invention, also applicable to bone screws in general, provision is made in the screw itself to control the placement and flow of bone cement.

Figure 9:
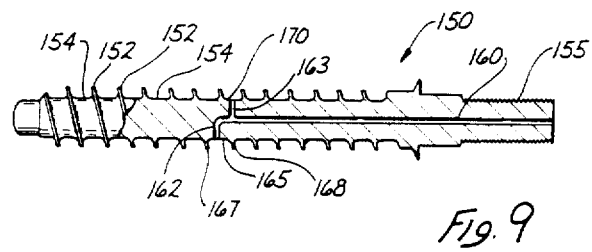
FIG. 9 is a sectional view of an improved cancellous bone screw in accordance with this invention which facilitates the use of bone cement.

Referring to FIG. 9, a typical bone screw 150 is illustrated, of the type described in U.S. Pat. No. 4,653,481, for example. Such a screw includes a helical thread composed of crests 152 and valleys 154 between adjacent crests along the threaded end of the screw. The axial dimension of the valleys is preferably greater than the axial dimension of the crests. On the other end 155, the mounting end, the configuration may vary depending upon what is to be mounted. The mounting end may be as described herein.

To achieve controlled flow and direction of the fluid bone cement, an aperture or bore 160 is provided axially along the length of the screw, the aperture being open on the mounting end 155. The aperture is preferably relatively small so as not to weaken the screw but of a dimension which will permit flow of the cement. In addition, two feed apertures 162 and 163 are provided, radially oriented, each of which is in fluid communication with aperture 160. These apertures may be slightly larger in diameter than the diameter of aperture 160. The apertures 162 and 163 are oriented 180 degrees with respect to each other and are axially offset such that one aperture opens into the valley 165 between crests 167 and 168 and the other 163 opens into valley 170 which is axially displaced from aperture 165 by one crest. It is preferred that the apertures 162 and 163 be located approximately near the mid-point axially along length of the threaded section.

Locating the apertures 162 and 163 in the valleys offers two advantages. First, the crests remain continuous and there are not crest discontinuities which might adversely affect the performance of the bone screw. Secondly, the valleys tend to form a conduit for controlled flow of the bone cement to the region between the screw and the surrounding bone structure.

In use, the bone screw is inserted and a hypodermic syringe containing bone cement is used to introduce the cement into the aperture 160, the cement flowing to and through apertures 165 and 170 and into the valleys between adjacent crests. By selecting a needle of the proper diameter, the end of the needle may be inserted into the open end of the bore and the bone cement can then be forced into the bore to cause the cement to flow down the aperture 160 to apertures 165 and 170. The cement then can flow axially along the valleys in each direction, and over the crests if the supporting bone structure permits, thereby effectively filling any open or less dense space between the outer surface of the screw and the adjacent bone structure. More importantly, however, the cement is effectively delivered only to the region where it is effective and needed, the annulus between the screw and the surrounding bone structure.

The cement delivery system above described may be used with a wide variety of bone screws of varying thread and valley configurations.

It is apparent from the foregoing detailed description that the present invention has many advantages over the prior art support systems. It is also apparent that various modifications may be made to the present invention by those skilled in the art without departing from the scope of the appended claims.

What is claimed is:

1. Segmental instrumentation of the posterior spine for providing additional internal support and adjustment during a fusion process in cases of spinal instability, comprising:
   threaded bone screws for threaded insertion into a bone structure,
   threaded adjusting rods,
   clevis means threaded on one end of said rod,
   intravertebral hook means threaded on the other end of said rod for reception on the lamina,
   each said bone screw including spaced engagement arms for receiving the clevis on the end of the adjusting rod in one relative position of the clevis with respect to the bone screw and for locking the clevis to the bone screw in all other relative positions thereof, and
   means on said threaded adjustment rods for increasing or decreasing the distance between the intravertebral hook means and the clevis for effecting compression or distraction.

2. Segmental instrumentation of the posterior spine as set forth in claim 1 wherein each of said clevis means and said intravertebral hook means are provided with sight apertures transversely thereof for assuring the position of the ends of the threaded adjustment rods.

3. Segmental instrumentation of the posterior spine as set forth in claim 1 wherein said bone screws are sacral bone screws for insertion into the sacrum at spaced locations, and
   the space between said sacrum screws being greater than the space between said hook means for providing added stability to the instrumentation.

4. Segmental instrumentation of the posterior spine as set forth in claim 1 wherein said hook means are distraction hooks, one having a left hand orientation and the other having a right hand orientation.

5. Segmental instrumentation of the posterior spine as set forth in claim 1 wherein said threaded adjusting rods include left hand threads on one end thereof and right hand threads on the other end thereof.

6. Segmental instrumentation of the posterior spine as set forth in claim 1 wherein said clevis means includes a pivot pin rotatable relative to said clevis means.

7. Segmental instrumentation of the posterior spine as set forth in claim 6 wherein said spaced engagement arms include compound track means for receiving the pivot pin of said clevis means.

8. A self locking bone screw and clevis assembly for use as implantable instrumentation for support and stabilization of the spine, and the like, comprising a bone screw having a threaded portion and a mounting portion, clevis means adapted to be received in locking relation on the mounting portion of said bone screw, said clevis means including a locking face, and pivot pin means defining the axis of rotation of said clevis means relative to the mounting portion of said bone screw, said mounting portion including spaced engagement arms to receive said pivot pin means of said clevis means, and locking face means located between said arms whereby said clevis means may be assembled to said mounting portion by aligning the locking face thereof with the locking face means and whereby said clevis means is locked to said mounting portion in all misaligned orientations of said locking face relative to said locking face means.

9. A self locking bone screw and clevis assembly as set forth in claim 8 wherein said mounting portion of said bone screw includes spaced engagement arms each having a compound track therein, said compound track including an open end and a locking track section, the open end including track faces which are in spaced parallel relation to said locking face means, and said locking track section including locking track faces oriented at an angle different from the angle of said track faces.

10. A bone screw for use with a clevis assembly for automatic locking of the clevis assembly thereto, comprising:

a threaded end adapted to be inserted into a bone structure and a mounting end adapted to receive a clevis assembly, said mounting end including spaced arms and a locking face between said spaced arms, each of said arms including a slotted track of a compound configuration, each slotted track including an open end and opposed track faces at a predetermined angle, each slotted track further including a locking track face section inclined at an angle different from that of the track faces.

11. A pivotal clevis assembly for self-locking to a bone screw comprising:

a body section internally threaded to receive an externally threaded member, a clevis end including a pivot pin aperture, a pivot pin secured in said aperture and rotatable with respect to said clevis end, said clevis end including a first face and adjacent surfaces, and the dimension from the centerline of the pivot pin to said first face being less than the dimension from the centerline of the pivot pin to said adjacent surfaces.

12. A bone screw and clevis assembly for automatic locking of the clevis assembly thereto, comprising:

a bone screw having a threaded end adapted to be inserted into a bone structure and a mounting end adapted to receive a clevis assembly, said mounting end including spaced arms and a locking face between said spaced arms, each of said arms including a slotted track of a compound configuration, each slotted track including an open end and opposed track faces at a predetermined angle, each slotted track further including a locking track face section inclined at an angle different from that of the track faces, a pivotal clevis assembly including a body section internally threaded to receive an externally threaded member, a clevis end on said clevis assembly including a pivot pin aperture, a pivot pin secured in said aperture and rotatable with respect to said clevis end, said clevis end including a first face and adjacent surfaces, and the dimension from the centerline of the pivot pin to said first face being less than the dimension from the centerline of the pivot pin to said adjacent surfaces whereby said clevis assembly may be assembled to said mounting end of said screw by orienting said clevis assembly in one orientation and locking said clevis assembly by rotating the latter to an orientation other than said one orientation.

13. An improved bone screw for insertion into a bone structure during an implant and for use with a bone cement to secure said bone screw in place, comprising:

an axially extending threaded end portion including spaced crests with valleys therebetween, a portion adjacent said threaded portion adapted to receive instrumentation to be supported in place by said bone screw and terminating in and end face, axial aperture means extending through said end face and extending axially into an at least partly along the length of said axially extending threaded portion, transverse aperture means communicating with said axial aperture means whereby a bone cement may be inserted into axial aperture for flow axially and then transversely into the space, if any, between said bone screw and the surrounding bone structure for securing said bone screw to the surrounding bone structure, and said transverse aperture means including at least two axially spaced apertures located in a valley between an adjacent crest.

14. An improved bone screw for insertion into a bone structure as set forth in claim 13 wherein said axially spaced apertures are located 180 degrees with respect to each other.

* * * * *

UNITED STATES PATENT AND TRADEMARK OFFICE
CERTIFICATE OF CORRECTION

PATENT NO. : 5,034,011
DATED : July 23, 1991
INVENTOR(S) : Robert S. Howland

It is certified that error appears in the above-identified patent and that said Letters Patent is hereby corrected as shown below:

TITLE PAGE:

Replace current drawing with Figure 1 of Sheet 1, attached.

IN THE DRAWINGS:

Replace sheets 1 through 3, containing Figures 1 through 6 with correct sheets 1 through 3, containing Figures 1 through 9.

Signed and Sealed this

Thirteenth Day of April, 1993

*Attest:*

STEPHEN G. KUNIN

*Attesting Officer*     *Acting Commissioner of Patents and Trademarks*

United States Patent [19]

Howland

[11] Patent Number: 5,034,011

[45] Date of Patent: Jul. 23, 1991

[54] SEGMENTAL INSTRUMENTATION OF THE POSTERIOR SPINE

[75] Inventor: Robert S. Howland, Seal Beach, Calif.

[73] Assignee: Advanced Spine Fixation Systems Incorporated, Stanton, Calif.

[21] Appl. No.: 565,266

[22] Filed: Aug. 9, 1990

[51] Int. Cl.⁵ .......................... A61F 5/04; A61F 5/00; A61F 2/44
[52] U.S. Cl. ........................................ 606/61; 606/72; 606/73; 128/69; 623/17
[58] Field of Search ................ 606/61, 59, 57, 65, 606/72, 73, 105; 128/69; 623/16, 17

[56] References Cited

U.S. PATENT DOCUMENTS

| | | | |
|---|---|---|---|
| 4,361,141 | 11/1982 | Tanner | 128/69 |
| 4,382,438 | 5/1983 | Jacobs | 606/61 |
| 4,411,259 | 10/1983 | Drummonds | 606/61 |
| 4,422,451 | 12/1983 | Kalamchi | 128/69 |
| 4,433,677 | 2/1984 | Ulrich | 128/69 |
| 4,569,338 | 2/1986 | Edwards | 606/61 |
| 4,653,481 | 3/1987 | Howland | 128/69 |
| 4,655,199 | 4/1987 | Steffee | 606/61 |
| 4,771,767 | 9/1988 | Steffee | 606/61 |
| 4,854,304 | 8/1989 | Zielke | 128/69 |

FOREIGN PATENT DOCUMENTS 3802833 9/1988 Fed. Rep. of Germany ........ 606/61

Primary Examiner—Robert A. Hafer
Assistant Examiner—Michael Brown
Attorney, Agent, or Firm—Beehler & Pavitt

[57] ABSTRACT

Improved instrumentation of the posterior spine includes a threaded screw for insertion into the sacrum, threaded adjusting rods and intravertebral hook device on the end of the adjusting rod. One end of the adjusting rod includes a pivotal clevis assembly and an automatic safety interlock for securing the clevis assembly to the screw. The receiving end of the bone screw includes spaced arms to receive the clevis which is inserted and rotated to a locking position. Thereafter, the hooks are positioned on the lamina and the adjusting rod is adjusted for compression or distraction. The hex area on the adjusting rods are then safety wired. The generally triangular orientation provides added strength and a wider foot print attachment which will resist rotational forces. Also disclosed is an improved bone screw which facilitates placement of a bone cement in the desired location.

14 Claims, 3 Drawing Sheets

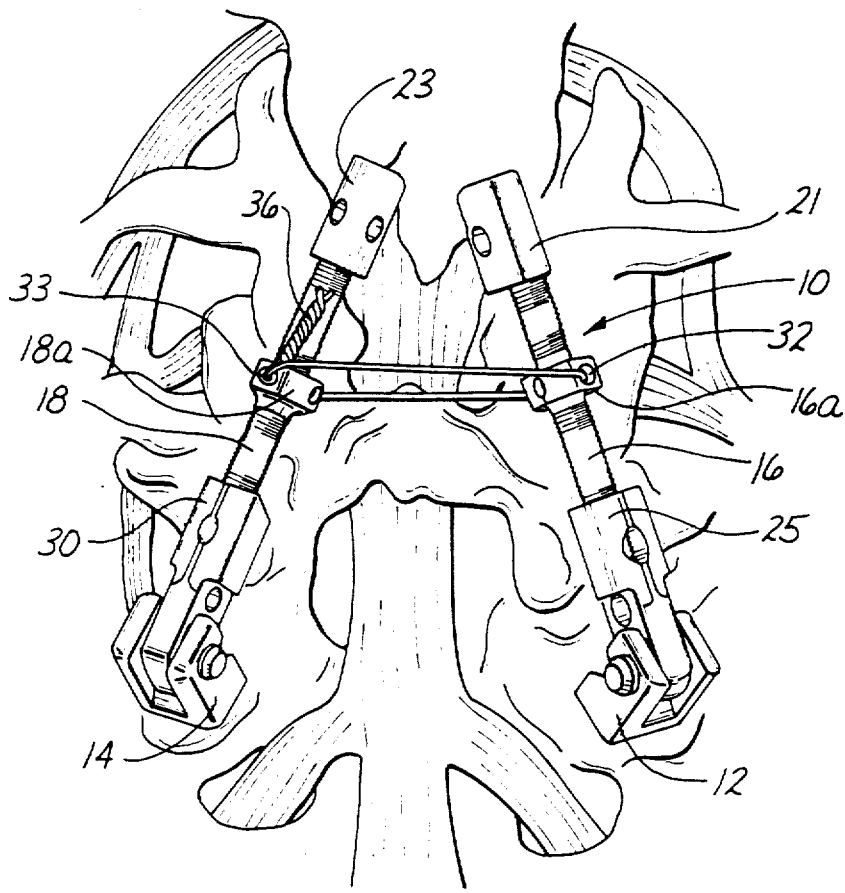

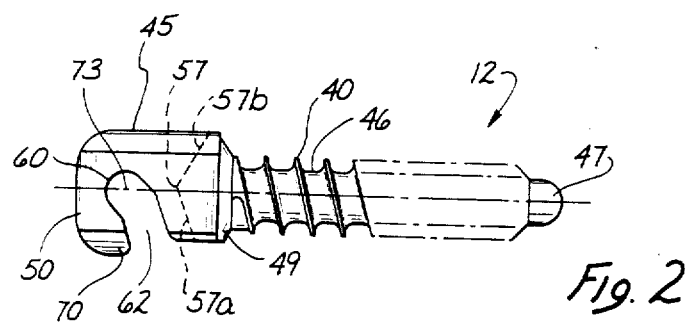
Fig. 2
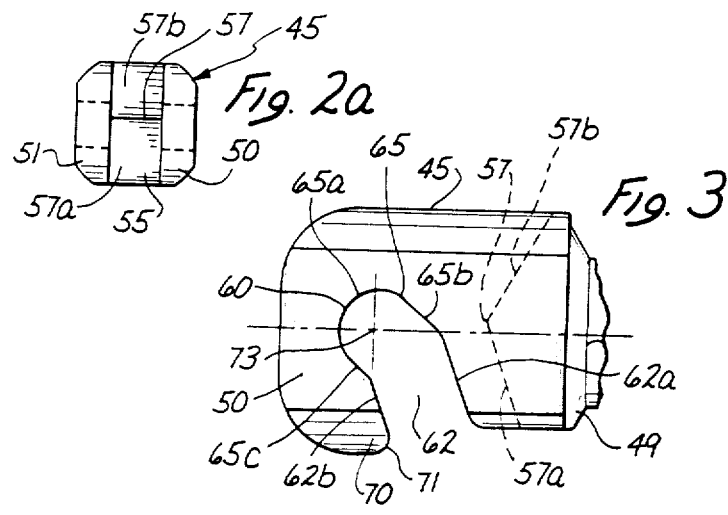
Fig. 2a
Fig. 3
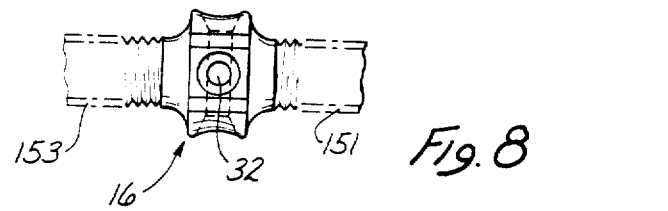
Fig. 8

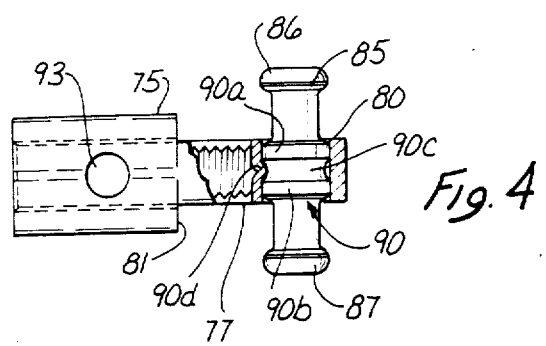
Fig. 4
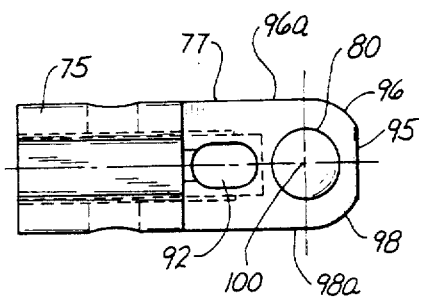
Fig. 5
Fig. 6
Fig. 7